(12) United States Patent
Gleave et al.

(10) Patent No.: US 7,196,067 B2
(45) Date of Patent: Mar. 27, 2007

(54) ANTISENSE INSULIN-LIKE GROWTH FACTOR BINDING PROTEIN (IGFBP)-2-OLIGODEOXYNUCLEOTIDES FOR PROSTATE AND OTHER ENDOCRINE TUMOR THERAPY

(75) Inventors: Martin Gleave, Vancouver (CA); Paul S. Rennie, Richmond (CA); Kiyama Satoshi, Yamatokoriyama (JP); Colleen Nelson, Surrey (CA)

(73) Assignee: The University of British Columbia, Vancouver (CA)

( * ) Notice: Subject to any disclaimer, the term of this patent is extended or adjusted under 35 U.S.C. 154(b) by 495 days.

(21) Appl. No.: 10/380,195

(22) PCT Filed: Sep. 13, 2001

(86) PCT No.: PCT/US01/28748

§ 371 (c)(1),
(2), (4) Date: Mar. 12, 2003

(87) PCT Pub. No.: WO02/22642

PCT Pub. Date: Mar. 21, 2002

(65) Prior Publication Data

US 2004/0072776 A1     Apr. 15, 2004

Related U.S. Application Data

(60) Provisional application No. 60/232,641, filed on Sep. 14, 2000.

(51) Int. Cl.
*A61K 31/70* (2006.01)
*C07H 21/04* (2006.01)

(52) U.S. Cl. .................................... 514/44; 536/24.5
(58) Field of Classification Search .................. None
See application file for complete search history.

(56) References Cited

U.S. PATENT DOCUMENTS 5,929,040 A * 7/1999 Werther et al. ............... 514/44
6,284,741 B1   9/2001 Werther et al.

FOREIGN PATENT DOCUMENTS

WO    WO 00/69454    11/2000

OTHER PUBLICATIONS

Steller, et al. Insulin-like growth factor II mediates epidermal growth factor-induced mitogenesis in cervical cancer cells. Proc. Natl. Acad. Sci., Dec. 1995, vol. 92, pp. 11970-11974.

Corkins et al. Growth Stimulation By Transfection of Intestinal Epithelial Cells With An Antisense Insulin-Like Growth Factor Binding Protein-2 Construct. Biochem. Biophys. Res. Com. Jun. 26, 1995, vol. 211, No. 3, pp. 707-713.

Wang, et al. Correlation of Glioma Cell Regression with Inhibition of Insulin-Like Growth Factor Binding Protein-2 Expression. Neuroendocrinology. 1997, vol. 66, pp. 203-211.

Bubendorf, et al., "*Hormone Therapy Failure in Human Prostate Cancer: Analysis by Complementary DNA and Tissue Microarrays*", Oct. 20, 1999, pp. 1758-1764, vol. 91, No. 20, Publisher: Journal of the National Cancer Institute; US Dept. of Health, Education and Welfare; Public Health, Published in: USA.

Forsyth, et al., "*Growth Inhibition of a Human Colon Cancer Cell Line by Antisense Oligonucleotide to IGFBP-2*", 1995, p. A726, vol. 108, No. 4, Publisher: Gastroenterology, Saunders, Published in: Philadelphia, PA, USA.

Gleave, et al., "*Antisense Targets to Enhance Hormone and Cytotoxic Therapies in Advanced Prostate Cancer*", 2003, pp. 209-221, vol. 4, No. 3, Publisher: Current Drug Targets; Bentham Science Publisher, Published in: USA.

Miyake, et al., "*Castration-Induced Up-Regulation of Insulin-Like Growth Factor Binding Protein-5 Potentiates Insulin-Like Growth Factor-I Activity and Accelerates Progression to Androgen Independence in Prostate Cancer Models*"; Jun. 1, 2000, pp. 3058-3064, Publisher: Cancer Research, American Association for Cancer Research, Published in: Baltimore, MD, USA.

Binkert, et al., "*Structure of the Human Insulin-Like Growth Factor Binding Protein-2 Gene*", 1992, pp. 826-836, vol. 6, No. 5, Publisher: Molecular Endocrinology, Published in: US.

* cited by examiner

*Primary Examiner*—James Schultz
*Assistant Examiner*—Tracy Vivlemore
(74) *Attorney, Agent, or Firm*—Marina Larson & Associates, LLC

(57) ABSTRACT

Compositions and a method are provided for the treatment of prostate and other endocrine tumors in mammals, including humans, by administration of an antisense oligodeoxynucleotide (ODN) which is complementary to a portion of the gene encoding IGFBP-2. Using the Shionogi tumor model in vitro and in vivo, the administration of such an ODN was shown to reduce proliferation of tumor cells, and also to delay the progression to androgen independence. Thus, treatment of prostate and other hormone-regulated cancer in mammals, including humans, and delay of the progression of prostate tumors to androgen independence is accomplished by administering to the mammal a therapeutically effective amount of an antisense oligodeoxynucleotide which is complementary to a portion of the nucleic acid sequence encoding IGFBP-2 and which reduces the amount of IGFBP-2 in the treated cells.

8 Claims, 5 Drawing Sheets

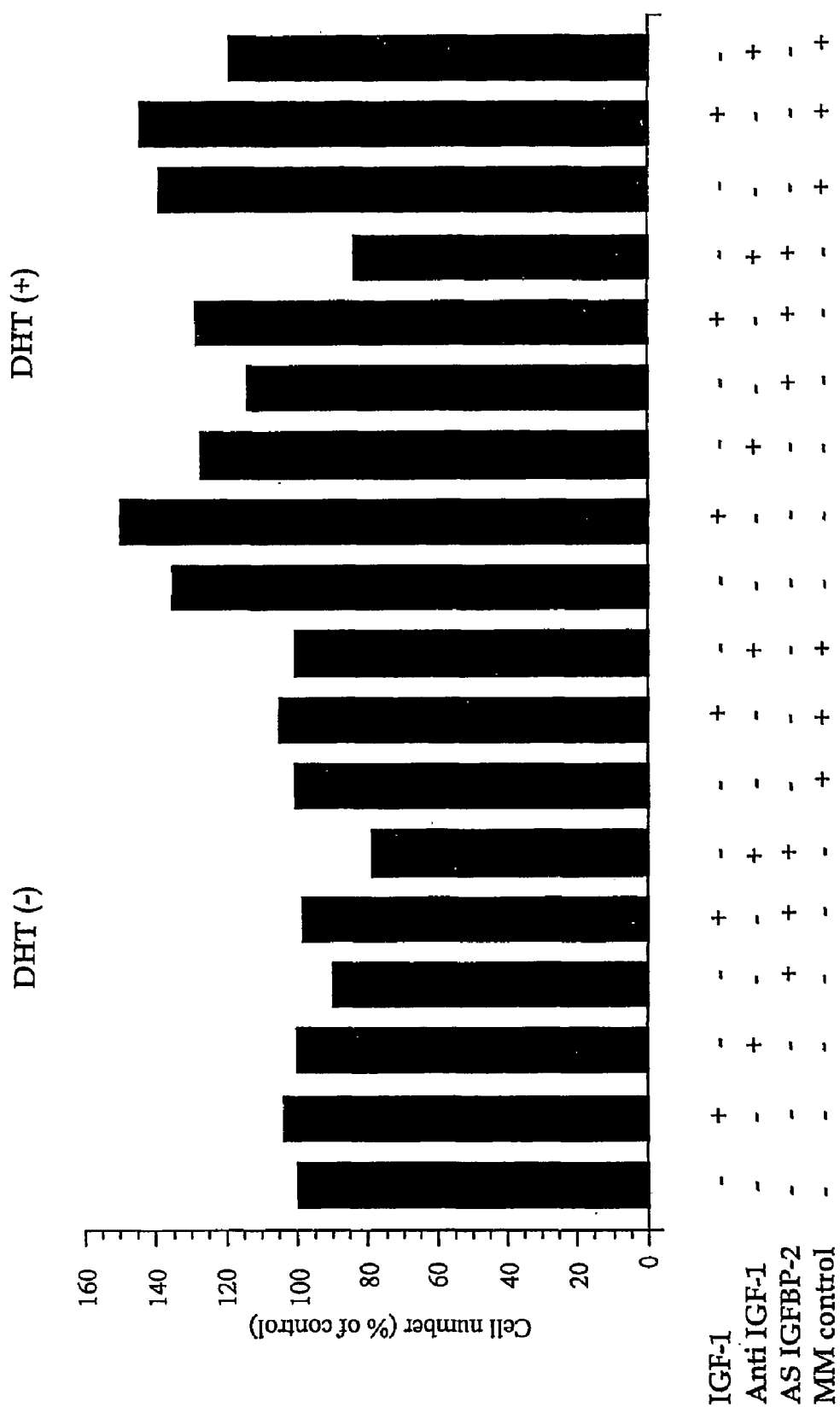

SEQUENCE LISTING

```
<160> NUMBER OF SEQ ID NOS: 63

<210> SEQ ID NO 1
<211> LENGTH: 21
<212> TYPE: DNA
<213> ORGANISM: Artificial Sequence
<220> FEATURE:
<223> OTHER INFORMATION: IGFBP2 antisense

<400> SEQUENCE: 1
gcagcccact ctcggcagca t                                    21

<210> SEQ ID NO 2
<211> LENGTH: 21
<212> TYPE: DNA
<213> ORGANISM: Artificial Sequence
<220> FEATURE:
<223> OTHER INFORMATION: IGFBP2 antisense

<400> SEQUENCE: 2
cgcccagtag cagcagcagc a                                    21

<210> SEQ ID NO 3
<211> LENGTH: 21
<212> TYPE: DNA
<213> ORGANISM: Artificial Sequence
<220> FEATURE:
<223> OTHER INFORMATION: IGFBP2 antisense

<400> SEQUENCE: 3
tcccggaaca cggccagctc c                                    21

<210> SEQ ID NO 4
<211> LENGTH: 20
<212> TYPE: DNA
<213> ORGANISM: Artificial Sequence
<220> FEATURE:
<223> OTHER INFORMATION: IGFBP2 antisense

<400> SEQUENCE: 4
cagcccactc tcggcagcat                                      20

<210> SEQ ID NO 5
<211> LENGTH: 20
<212> TYPE: DNA
<213> ORGANISM: Artificial Sequence
<220> FEATURE:
<223> OTHER INFORMATION: IGFBP2 antisense

<400> SEQUENCE: 5
```
gggcagcgga acagcacctc                                                 20

<210> SEQ ID NO 6
<211> LENGTH: 20
<212> TYPE: DNA
<213> ORGANISM: Artificial Sequence
<220> FEATURE:
<223> OTHER INFORMATION: IGFBP2 antisense

<400> SEQUENCE: 6
cccggctccc ggacgagctc                                                 20

<210> SEQ ID NO 7
<211> LENGTH: 20
<212> TYPE: DNA
<213> ORGANISM: Artificial Sequence
<220> FEATURE:
<223> OTHER INFORMATION: IGFBP2 antisense

<400> SEQUENCE: 7
gcctgcaggg gcagctcgga                                                 20

<210> SEQ ID NO 8
<211> LENGTH: 20
<212> TYPE: DNA
<213> ORGANISM: Artificial Sequence
<220> FEATURE:
<223> OTHER INFORMATION: IGFBP2 antisense

<400> SEQUENCE: 8
acgtggttct ccaccaggcc                                                 20

<210> SEQ ID NO 9
<211> LENGTH: 20
<212> TYPE: DNA
<213> ORGANISM: Artificial Sequence
<220> FEATURE:
<223> OTHER INFORMATION: IGFBP2 antisense

<400> SEQUENCE: 9
cccatctgcc ggtgctgctc                                                 20

<210> SEQ ID NO 10
<211> LENGTH: 20
<212> TYPE: DNA
<213> ORGANISM: Artificial Sequence
<220> FEATURE:
<223> OTHER INFORMATION: IGFBP2 antisense

<400> SEQUENCE: 10
aggcgcatgg tggagatccg                                                 20

<210> SEQ ID NO 11
<211> LENGTH: 20
<212> TYPE: DNA
<213> ORGANISM: Artificial Sequence
<220> FEATURE:
<223> OTHER INFORMATION: IGFBP2 antisense

<400> SEQUENCE: 11
cactccccac gctgcccgtt                                                 20

<210> SEQ ID NO 12
<211> LENGTH: 20
<212> TYPE: DNA

```
<213> ORGANISM: Artificial Sequence
<220> FEATURE:
<223> OTHER INFORMATION: IGFBP2 antisense

<400> SEQUENCE: 12
cgctgggtgt gcaccccgcg                                                     20

<210> SEQ ID NO 13
<211> LENGTH: 20
<212> TYPE: DNA
<213> ORGANISM: Artificial Sequence
<220> FEATURE:
<223> OTHER INFORMATION: IGFBP2 antisense

<400> SEQUENCE: 13
tgtcagaact ggaaaatcct                                                     20

<210> SEQ ID NO 14
<211> LENGTH: 21
<212> TYPE: DNA
<213> ORGANISM: Artificial Sequence
<220> FEATURE:
<223> OTHER INFORMATION: IGFBP2 antisense

<400> SEQUENCE: 14
gcagcccact ctcggcagca t                                                   21

<210> SEQ ID NO 15
<211> LENGTH: 21
<212> TYPE: DNA
<213> ORGANISM: Artificial Sequence
<220> FEATURE:
<223> OTHER INFORMATION: IGFBP2 antisense

<400> SEQUENCE: 15
cagtagcagc agcagcagcg g                                                   21

<210> SEQ ID NO 16
<211> LENGTH: 21
<212> TYPE: DNA
<213> ORGANISM: Artificial Sequence
<220> FEATURE:
<223> OTHER INFORMATION: IGFBP2 antisense

<400> SEQUENCE: 16
tgtgcagggc gggcagcgga a                                                   21

<210> SEQ ID NO 17
<211> LENGTH: 21
<212> TYPE: DNA
<213> ORGANISM: Artificial Sequence
<220> FEATURE:
<223> OTHER INFORMATION: IGFBP2 antisense

<400> SEQUENCE: 17
gccctccagc cgggcgcaca c                                                   21

<210> SEQ ID NO 18
<211> LENGTH: 21
<212> TYPE: DNA
<213> ORGANISM: Artificial Sequence
<220> FEATURE:
<223> OTHER INFORMATION: IGFBP2 antisense

<400> SEQUENCE: 18
gcccgggtgg ggatagcagc g                                                   21
```

<210> SEQ ID NO 19
<211> LENGTH: 21
<212> TYPE: DNA
<213> ORGANISM: Artificial Sequence
<220> FEATURE:
<223> OTHER INFORMATION: IGFBP2 antisense

<400> SEQUENCE: 19
cgcctgcagg ggcagctcgg a                                          21

<210> SEQ ID NO 20
<211> LENGTH: 21
<212> TYPE: DNA
<213> ORGANISM: Artificial Sequence
<220> FEATURE:
<223> OTHER INFORMATION: IGFBP2 antisense

<400> SEQUENCE: 20
agtgccctcg cccatgacca g                                          21

<210> SEQ ID NO 21
<211> LENGTH: 21
<212> TYPE: DNA
<213> ORGANISM: Artificial Sequence
<220> FEATURE:
<223> OTHER INFORMATION: IGFBP2 antisense

<400> SEQUENCE: 21
ctccgggctg gcgccatact c                                          21

<210> SEQ ID NO 22
<211> LENGTH: 21
<212> TYPE: DNA
<213> ORGANISM: Artificial Sequence
<220> FEATURE:
<223> OTHER INFORMATION: IGFBP2 antisense

<400> SEQUENCE: 22
atcgccattg tctgcaacct g                                          21

<210> SEQ ID NO 23
<211> LENGTH: 21
<212> TYPE: DNA
<213> ORGANISM: Artificial Sequence
<220> FEATURE:
<223> OTHER INFORMATION: IGFBP2 antisense

<400> SEQUENCE: 23
caggcctcct tctgagtggt c                                          21

<210> SEQ ID NO 24
<211> LENGTH: 21
<212> TYPE: DNA
<213> ORGANISM: Artificial Sequence
<220> FEATURE:
<223> OTHER INFORMATION: IGFBP2 antisense

<400> SEQUENCE: 24
gctgtccacg tggttctcca c                                          21

<210> SEQ ID NO 25
<211> LENGTH: 21
<212> TYPE: DNA
<213> ORGANISM: Artificial Sequence
<220> FEATURE:

```
<223> OTHER INFORMATION: IGFBP2 antisense

<400> SEQUENCE: 25
cccgcccaac atgttcatgg t                                              21

<210> SEQ ID NO 26
<211> LENGTH: 21
<212> TYPE: DNA
<213> ORGANISM: Artificial Sequence
<220> FEATURE:
<223> OTHER INFORMATION: IGFBP2 antisense

<400> SEQUENCE: 26
cttccggcca gcactgcctc c                                              21

<210> SEQ ID NO 27
<211> LENGTH: 21
<212> TYPE: DNA
<213> ORGANISM: Artificial Sequence
<220> FEATURE:
<223> OTHER INFORMATION: IGFBP2 antisense

<400> SEQUENCE: 27 cttcatacccc gacttgaggg g                                             21

<210> SEQ ID NO 28
<211> LENGTH: 21
<212> TYPE: DNA
<213> ORGANISM: Artificial Sequence
<220> FEATURE:
<223> OTHER INFORMATION: IGFBP2 antisense

<400> SEQUENCE: 28
ctcccggaac acggccagct c                                              21

<210> SEQ ID NO 29
<211> LENGTH: 21
<212> TYPE: DNA
<213> ORGANISM: Artificial Sequence
<220> FEATURE:
<223> OTHER INFORMATION: IGFBP2 antisense

<400> SEQUENCE: 29
ccggtgctgc tcagtgacct t                                              21

<210> SEQ ID NO 30
<211> LENGTH: 21
<212> TYPE: DNA
<213> ORGANISM: Artificial Sequence
<220> FEATURE:
<223> OTHER INFORMATION: IGFBP2 antisense

<400> SEQUENCE: 30
cttgccaccc ttgcccatct g                                              21

<210> SEQ ID NO 31
<211> LENGTH: 21
<212> TYPE: DNA
<213> ORGANISM: Artificial Sequence
<220> FEATURE:
<223> OTHER INFORMATION: IGFBP2 antisense

<400> SEQUENCE: 31
ctcctccagg ccaaggtgat g                                              21
```

```
<210> SEQ ID NO 32
<211> LENGTH: 21
<212> TYPE: DNA
<213> ORGANISM: Artificial Sequence
<220> FEATURE:
<223> OTHER INFORMATION: IGFBP2 antisense

<400> SEQUENCE: 32
gggtggtcgc agcttcttgg g                                              21

<210> SEQ ID NO 33
<211> LENGTH: 21
<212> TYPE: DNA
<213> ORGANISM: Artificial Sequence
<220> FEATURE:
<223> OTHER INFORMATION: IGFBP2 antisense

<400> SEQUENCE: 33
ttggcaggga gtcctggcag g                                              21

<210> SEQ ID NO 34
<211> LENGTH: 21
<212> TYPE: DNA
<213> ORGANISM: Artificial Sequence
<220> FEATURE:
<223> OTHER INFORMATION: IGFBP2 antisense

<400> SEQUENCE: 34
caggacctgg tccagttcct g                                              21

<210> SEQ ID NO 35
<211> LENGTH: 21
<212> TYPE: DNA
<213> ORGANISM: Artificial Sequence
<220> FEATURE:
<223> OTHER INFORMATION: IGFBP2 antisense

<400> SEQUENCE: 35
gcgcatggtg gagatccgct c                                              21

<210> SEQ ID NO 36
<211> LENGTH: 21
<212> TYPE: DNA
<213> ORGANISM: Artificial Sequence
<220> FEATURE:
<223> OTHER INFORMATION: IGFBP2 antisense

<400> SEQUENCE: 36
agggccccgc tcatccggaa g                                              21

<210> SEQ ID NO 37
<211> LENGTH: 21
<212> TYPE: DNA
<213> ORGANISM: Artificial Sequence
<220> FEATURE:
<223> OTHER INFORMATION: IGFBP2 antisense

<400> SEQUENCE: 37
cagggagtag aggtgctcca g                                              21

<210> SEQ ID NO 38
<211> LENGTH: 21
<212> TYPE: DNA
<213> ORGANISM: Artificial Sequence
<220> FEATURE:
<223> OTHER INFORMATION: IGFBP2 antisense
```

-continued

<400> SEQUENCE: 38
cttgtcacag ttggggatgt g                                               21

<210> SEQ ID NO 39
<211> LENGTH: 21
<212> TYPE: DNA
<213> ORGANISM: Artificial Sequence
<220> FEATURE:
<223> OTHER INFORMATION: IGFBP2 antisense

<400> SEQUENCE: 39
tttgaggttg tacaggccat g                                               21

<210> SEQ ID NO 40
<211> LENGTH: 21
<212> TYPE: DNA
<213> ORGANISM: Artificial Sequence
<220> FEATURE:
<223> OTHER INFORMATION: IGFBP2 antisense

<400> SEQUENCE: 40
gttcagagac atcttgcact g                                               21

<210> SEQ ID NO 41
<211> LENGTH: 21
<212> TYPE: DNA
<213> ORGANISM: Artificial Sequence
<220> FEATURE:
<223> OTHER INFORMATION: IGFBP2 antisense

<400> SEQUENCE: 41
ccagcactcc ccacgctgcc c                                               21

<210> SEQ ID NO 42
<211> LENGTH: 21
<212> TYPE: DNA
<213> ORGANISM: Artificial Sequence
<220> FEATURE:
<223> OTHER INFORMATION: IGFBP2 antisense

<400> SEQUENCE: 42
cccggtgttg gggttcacac a                                               21

<210> SEQ ID NO 43
<211> LENGTH: 21
<212> TYPE: DNA
<213> ORGANISM: Artificial Sequence
<220> FEATURE:
<223> OTHER INFORMATION: IGFBP2 antisense

<400> SEQUENCE: 43
gggggctccc tggatcagct t                                               21

<210> SEQ ID NO 44
<211> LENGTH: 21
<212> TYPE: DNA
<213> ORGANISM: Artificial Sequence
<220> FEATURE:
<223> OTHER INFORMATION: IGFBP2 antisense

<400> SEQUENCE: 44
ctcggggtcc ccccggatgg t                                               21

<210> SEQ ID NO 45
<211> LENGTH: 21

```
<212> TYPE: DNA
<213> ORGANISM: Artificial Sequence
<220> FEATURE:
<223> OTHER INFORMATION: IGFBP2 antisense

<400> SEQUENCE: 45
ctcattgtag aagagatgac a                                              21

<210> SEQ ID NO 46
<211> LENGTH: 21
<212> TYPE: DNA
<213> ORGANISM: Artificial Sequence
<220> FEATURE:
<223> OTHER INFORMATION: IGFBP2 antisense

<400> SEQUENCE: 46
cgcccagtag cagcagcagc a                                              21

<210> SEQ ID NO 47
<211> LENGTH: 21
<212> TYPE: DNA
<213> ORGANISM: Artificial Sequence
<220> FEATURE:
<223> OTHER INFORMATION: IGFBP2 antisense

<400> SEQUENCE: 47
tcccggaaca cggccagctc c                                              21

<210> SEQ ID NO 48
<211> LENGTH: 20
<212> TYPE: DNA
<213> ORGANISM: Artificial Sequence
<220> FEATURE:
<223> OTHER INFORMATION: IGFBP2 antisense

<400> SEQUENCE: 48
cagcccactc tcggcagcat                                                20

<210> SEQ ID NO 49
<211> LENGTH: 20
<212> TYPE: DNA
<213> ORGANISM: Artificial Sequence
<220> FEATURE:
<223> OTHER INFORMATION: IGFBP2 antisense

<400> SEQUENCE: 49
gggcagcgga acagcacctc                                                20

<210> SEQ ID NO 50
<211> LENGTH: 20
<212> TYPE: DNA
<213> ORGANISM: Artificial Sequence
<220> FEATURE:
<223> OTHER INFORMATION: IGFBP2 antisense

<400> SEQUENCE: 50
cccggctccc ggacgagctc                                                20

<210> SEQ ID NO 51
<211> LENGTH: 20
<212> TYPE: DNA
<213> ORGANISM: Artificial Sequence
<220> FEATURE:
<223> OTHER INFORMATION: IGFBP2 antisense

<400> SEQUENCE: 51
```
acgtggttct ccaccaggcc                                          20

<210> SEQ ID NO 52
<211> LENGTH: 20
<212> TYPE: DNA
<213> ORGANISM: Artificial Sequence
<220> FEATURE:
<223> OTHER INFORMATION: IGFBP2 antisense

<400> SEQUENCE: 52
cccatctgcc ggtgctgctc                                          20

<210> SEQ ID NO 53
<211> LENGTH: 20
<212> TYPE: DNA
<213> ORGANISM: Artificial Sequence
<220> FEATURE:
<223> OTHER INFORMATION: IGFBP2 antisense

<400> SEQUENCE: 53
aggcgcatgg tggagatccg                                          20

<210> SEQ ID NO 54
<211> LENGTH: 20
<212> TYPE: DNA
<213> ORGANISM: Artificial Sequence
<220> FEATURE:
<223> OTHER INFORMATION: IGFBP2 antisense

<400> SEQUENCE: 54
cactccccac gctgcccgtt                                          20

<210> SEQ ID NO 55
<211> LENGTH: 20
<212> TYPE: DNA
<213> ORGANISM: Artificial Sequence
<220> FEATURE:
<223> OTHER INFORMATION: IGFBP2 antisense

<400> SEQUENCE: 55
cgctgggtgt gcaccccgcg                                          20

<210> SEQ ID NO 56
<211> LENGTH: 20
<212> TYPE: DNA
<213> ORGANISM: Artificial Sequence
<220> FEATURE:
<223> OTHER INFORMATION: IGFBP2 antisense

<400> SEQUENCE: 56
tgtcagaact ggaaaatcct                                          20

<210> SEQ ID NO 57
<211> LENGTH: 21
<212> TYPE: DNA
<213> ORGANISM: Artificial Sequence
<220> FEATURE:
<223> OTHER INFORMATION: IGFBP2 mismatch antisense

<400> SEQUENCE: 57
gcagcccact gtccgcagca t                                        21

<210> SEQ ID NO 58
<211> LENGTH: 21
<212> TYPE: DNA
<213> ORGANISM: Artificial Sequence

```
<220> FEATURE:
<223> OTHER INFORMATION: IGFBP2 mismatch antisense

<400> SEQUENCE: 58
cgcgcactag cagcagcagc a                                          21

<210> SEQ ID NO 59
<211> LENGTH: 21
<212> TYPE: DNA
<213> ORGANISM: Artificial Sequence
<220> FEATURE:
<223> OTHER INFORMATION: IGFBP2 mismatch antisense

<400> SEQUENCE: 59
tcccggaact gccccagctc c                                          21

<210> SEQ ID NO 60
<211> LENGTH: 23
<212> TYPE: DNA
<213> ORGANISM: artificial
<220> FEATURE:
<223> OTHER INFORMATION: Northern Blot Probe

<400> SEQUENCE: 60
acaatggcgg atgaccactc aga                                        23

<210> SEQ ID NO 61
<211> LENGTH: 21
<212> TYPE: DNA
<213> ORGANISM: artificial
<220> FEATURE:
<223> OTHER INFORMATION: Northern Blot Probe

<400> SEQUENCE: 61
acagcaccat gaacatgttt g                                          21

<210> SEQ ID NO 62
<211> LENGTH: 21
<212> TYPE: DNA
<213> ORGANISM: artificial
<220> FEATURE:
<223> OTHER INFORMATION: Northern Blot Probe

<400> SEQUENCE: 62
tgcttttaac tctggtaaag t                                          21

<210> SEQ ID NO 63
<211> LENGTH: 22
<212> TYPE: DNA
<213> ORGANISM: artificial
<220> FEATURE:
<223> OTHER INFORMATION: Northern Blot Probe

<400> SEQUENCE: 63
atatttggca ggttttctcta ga                                        22
```

ANTISENSE INSULIN-LIKE GROWTH FACTOR BINDING PROTEIN (IGFBP)-2-OLIGODEOXYNUCLEOTIDES FOR PROSTATE AND OTHER ENDOCRINE TUMOR THERAPY

This application is a Section 371 national stage of PCT/US01/28748 which claims the benefit of U.S. Provisional Application 60/232,641 filed Sep. 14, 2000.

FIELD OF THE INVENTION

The present invention relates generally to antisense oligonucleotide therapy for cancer. More specifically, prostate and breast cancer are targeted.

BACKGROUND OF THE INVENTION

This application relates to the treatment of prostate tumors making use of an antisense oligonucleotide that has a sequence complementary to the sequence encoding insulin-like growth factor binding protein (IGFBP)-2.

Prostate cancer is the most common cancer that affects men, and the second leading cause of cancer death in men in the Western world. Because prostate cancer is an androgen-sensitive tumor, androgen withdrawal, for example via castration, is utilized in some therapeutic regimens for patients with advanced prostate cancer. Androgen withdrawal leads to extensive apoptosis in the prostate tumor, and hence to a regression of the disease. However, castration-induced apoptosis is not complete, and a progression of surviving tumor cells to androgen-independence ultimately occurs. This progression is the main obstacle to improving survival and quality of life, and efforts have therefore been made to target androgen-independent cells. These efforts have focused on non-hormonal therapies targeted against androgen-independent tumor cells; however, no non-hormonal agent has improved survival thus far (Oh et al., *J. Urol* 160: 1220–1229 (1998)). Alternative approaches are therefore indicated. Recent studies in our laboratory suggest that increased levels of IGFBP-5 (Miyake et al, *Endocrinology* 141:2257–2265, (2000)) and IGFBP-2 after androgen ablation enhance IGF-1 mitogenesis and cell survival, thereby accelerating progression to androgen ablation.

Insulin-like growth factor (IGF)-I and IGF-II are potent mitogens for many normal and malignant cells. Accumulating evidence suggests that IGFs play an important role in the pathophysiology of prostatic disease and breast cancer (Boudon et al., *J. Clin. Endocrin. Metab.* 81: 612–617 (1996); Angelloz-Nicoud et al., *Endocrinology* 136: 5485–5492 (1995); Nickerson et al., *Endocrinology* 139: 807–810 (1998); Figueroa et al., *J. Urol.* 159: 1379–1383 (1998)).

The biological response to IGF's is regulated by various factors, including IGFBPs. To date, six IGFBPs have been identified whose function is believed to involve modulation of the biological actions of the IGFs through high affinity interactions (Rajaram et al. *Endocrin. Rev.* 18: 801–813 (1997)). However, some evidence suggests biological activity for IGFBPs that are independent of IGPs (Andress et al., J. Biol. Chem. 267: 22467–22472 (1992); Oh et al., J. Biol. Chem. 268: 14964–14971 (1993)), and both stimulatory and inhibitory effects of IGFBPs on cell proliferation have been reported under various experimental conditions (Andress et al., supra; Elgin et al., *Proc. Nat'l. Acad. Sci.* (*USA*), 84: 3254–3258 (1987); Huynh et al., *J. Biol. Chem.* 271: 1016–1021 (1996); Damon et al., *Endocrinology* 139: 3456–3464 (1998)). Thus, the precise function of IGFBPs remains controversial. Because of this, while the reported results implicate IGF in prostate cancer, they do not clearly suggest a therapeutic approach based upon this involvement.

The present invention utilizes antisense oligodeoxynucleotides (ODNs) targeted to IGFBP-2 as a treatment for prostate and other endocrine cancers. Antisense ODNs are stretches of single-stranded DNA that are complementary to mRNA regions of a target gene, and thereby effectively inhibit gene expression by forming RNA/DNA duplexes (Figueroa et al., *J. Urol.,* 159: 1379–1383 (1998)). Phosphorothioate ODNs are stabilized to resist nuclease digestion by substituting one of the nonbridging phosphoryl oxygens of DNA with a sulfur. Recently, several antisense ODNs specifically targeted against genes involved in neoplastic progression have been evaluated both in vitro and in vivo, and demonstrated the efficacy of antisense strategy as potential therapeutic agents (Monia et al., *Nature Med.* 2: 668–675 (1996); Cucco et al., *Cancer Res.* 56: 4332–4337 (1996); Ziegler et al., *J. Natl. Cancer Inst.* 89: 1027–1036 (1997); Jansen et al., *Nature Med.* 4: 232–234 (1998)).

SUMMARY OF THE INVENTION

In accordance with the invention, compositions and a method are provided for the treatment of prostate and other endocrine tumors in mammals, including humans, by administration of an antisense oligodeoxynucleotide (ODN) which is complementary to a portion of the gene encoding IGFBP-2. Using the androgen-sensitive human prostate cancer LNCaP and androgen-dependent murine Shionogi tumor model in vitro and in vivo, the administration of such an ODN was shown to reduce proliferation of tumor cells, and also to delay the progression to androgen independence. Thus, treatment of prostate cancer and other hormone-regulated cancers in mammals, including humans, and delay of the progression of prostate tumors to androgen independence is accomplished by administering to the mammal a therapeutically effective amount of an antisense oligodeoxynucleotide which is complementary to a portion of the nucleic acid sequence encoding IGFBP-2 and which results in a reduction of IGFBP-2 levels in the target cancer cells.

BRIEF DESCRIPTION OF THE FIGURES

FIG. 4 shows that treatment of human LNCaP tumor cells with IGFBP-2 ASO's resulted in greater than 50% growth inhibition in a time- and dose-dependent manner.

DETAILED DESCRIPTION OF THE INVENTION

Figure 1:
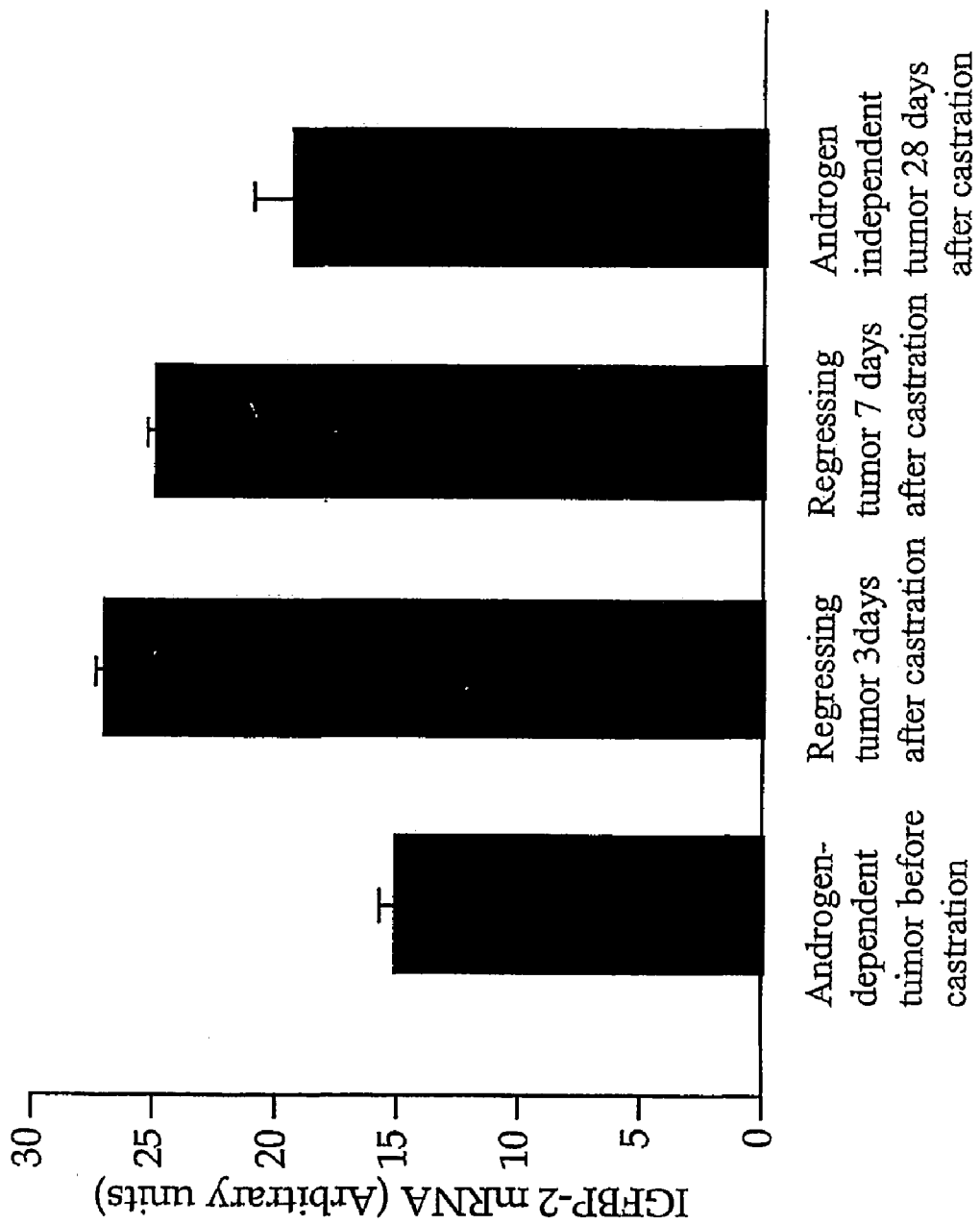
FIG. 1 shows densitometry traces for Northern analysis demonstrating increased IGFBP-2 mRNA levels in LNCaP cells after castration and during androgen-independent progression.

The present invention provides a method for delaying the progression of prostatic tumor cells to androgen independence, a therapeutic method for the treatment of individuals, including humans, suffering from hormone-regulated cancer such as prostate or breast cancer, and therapeutic agents effective for use in such methods. In addition, the compositions of the invention can be used to inhibit or delay the growth and metastatic progression of such cancers. The therapeutic method of the invention will most commonly be used in the treatment of individuals with advanced prostate cancer, but may also be used in conjunction with hormonal therapies of other endocrine malignancies, such as breast cancer.

In accordance with the first embodiment of the invention, the progression of androgen-sensitive prostatic cancer cells to androgen independence can be delayed by reducing the amount of IGFBP-2 in the cells. Experiments were performed in vitro and in vivo in the androgen-sensitive human prostate cancer LNCaP and androgen-dependent murine Shionogi tumor models. The Shionogi tumor model is a xenograft of an androgen dependent mouse mammary carcinoma that grows subcutaneously in male syngeneic hosts. Shionogi tumor cells are highly tumorigenic and locally invasive. The cells have been shown to respond to androgen withdrawal in a manner which mimics the observed behavior of prostatic tumor cells, and have been accepted as a valid model for prostate cancer in humans (Bruchovsky et al., *Cancer Res.* 50: 2275–2282 (1990); Rennie et al., *Cancer Res.* 48: 6309–6312 (1988); Bruchovsky et al., *Cell* 13: 272–280 (1978); Gleave et al., in *Genitourinary Oncology*, pp. 367–378, Lange et al. eds., Lippencott (1997); Gleave et al., *J. Urol.* 157: 1727–1730 (1997); Bruchovsky et al., *The Prostate* 6: 13–21 (1996)). Thus, androgen withdrawal precipitates apoptosis and tumor regression in a highly reproducible manner. Further, changes in expression and peptides such as TRPM-2 and Bcl-2 in human prostate cancer following castration and during progression to androgen-independence are similar to those observed in Shionogi tumor cells. Because of these similarities, the Shionogi tumor model mimics human prostate cancer and provides a very useful model for the evaluation of the ability of compounds to delay the onset of androgen-independence. Despite complete tumor regression after castration, rapidly growing androgen-independent Shionogi tumors invariably recur after one month, which provides a reliable end point to evaluate agents which can delay the progression to androgen-independence.

In the study leading to the present invention, we initially characterized the changes of IGFBP expression in the Shionogi tumor model after castration and during AI progression. Northern blot analyses were used to characterize changes in IGFBP mRNA expression in AD intact tumors before castration, regressing tumors 4 and 7 days after castration, and AI recurrent tumors 28 days after castration. Various patterns of changes in IGFBP-2, -3, -4, and -5 mRNA expression were observed. IGFBP-1 and IGFBP-6 mRNAs are undetectable in the Shionogi tumor model.

Northern blotting was used to characterize changes in IGFBP-2 mRNA expression in AD intact LNCaP tumors before castration and at various time points after castration. As shown in FIG. 1, IGFBP-2 expression increased gradually beginning 14 days after castration, and by 28 days after castration was >2-fold compared to levels before castration (two-sided p<0.05, student's t). Increased IGFBP-2 levels after castration was also identified using LNCAP and human prostate cancer tumor tissue microarrays. Mean IGFBP-2 staining intensity increased from +1 in AD tumors (n=20 spots) before castration to +2.3 in AI tumors (n=40 spots, 28 and 35 days after castration). The mean intensities of other groups were +1 for 3 days, +1.2 for 5, 7 and 10 days, +1.4 for 14 days, and +1.6 for 21 days after castration. Immunohistochemical staining results generally corresponded with results from Northern blotting.

In accordance with the present invention, antisense ODN's which are complementary to the sequence encoding IGFBP-2 are administered. When the subject is human, the sequence administered is based on human IGFBP-2. Specific antisense ODN are listed in Table 2 and are identified as Seq. ID Nos. 1–56. Seq. ID. No. 1 which includes the translation initiation site was the most active of those tested, and was used in the majority of the experiments reported herein. The ODNs employed maybe modified to increase the stability of the ODN in vivo. For example, the ODNs may be employed as phosphorothioate derivatives (replacement of a non-bridging phosphoryl oxygen atom with a sulfur atom) which have increased resistance to nuclease digestion. Increased ODN stability can also be achieved using molecules with 2-methoxyethyl substituted backbones.

Administration of antisense ODNs can be carried out using the various mechanisms known in the art, including naked administration and administration in pharmaceutically acceptable carriers. For example, lipid carriers for antisense delivery are described in U.S. Pat. Nos. 5,855,911 and 5,417,978 which are incorporated herein by reference. In general, the antisense is administered by intravenous, intraperitoneal, subcutaneous or oral routes.

The amount of antisense ODN administered is one effective to reduce the levels of IGFBP-2 in prostatic cells or other hormone-regulated tumor cells. In the context of the present invention, applicants do not intend to be bound by any specific mechanism by which this reduction may occur, although it is noted that the reduction may occur as a result of reduced expression of IGFBP-2 if the antisense molecule interferes with translation of the mRNA, or via an RNase mediated mechanism. Furthermore, it will be appreciated that the appropriate therapeutic amount will vary both with the effectiveness of the specific antisense ODN employed, and with the nature of any carrier used. The determination of appropriate amounts for any given composition is within the skill in the art, through standard series of tests designed to assess appropriate therapeutic levels.

The method for treating prostate cancer in accordance with the invention may further include administration of chemotherapy agents and/or additional antisense ODNs directed at different targets. For example, conventional chemotherapy agents such as taxol (paclitaxel or docetaxel) and mitoxanthrone may be used. Similarly, combinations of antisense IGFBP-2 ODN with other antisense sequences such as antisense Bcl-2 ODN, TRPM-2 ODN, or IGFBP-5 ODN may be used.

EXAMPLES

The invention will now be further described with reference to the following, non-limiting examples.

Example 1

Three oligonucleotides were prepared with the sequences given in Seq. ID. Nos. 1–3. Seq. ID No. 1 spans the translation initiation site of the IGFBP-2 mRNA starting with base number 64. Seq. ID Nos. 2 and 3 correspond to bases 131–151 and 630–650 respectively. Two base IGFBP-2 mismatch oligonucleotides (Seq. ID Nos. 57–59) were also prepared as controls.

Initial screening on these three oligonucleotides was done using LNCAP cells. Lipofectin, a cationic lipid (Life Technologies Inc. Gaithersburg, Md.) was used to increase uptake of the oligonucleotides into the cells. LNCaP cells were treated with one of the three oligonucleotides (Seq. ID. Nos. 1–3), 1000 nM, or the corresponding mismatch control (Seq. ID Nos. 57–59). Total RNA was extracted and analyzed by Northern Blot analysis for levels of IGFBP-2 encoding RNA. Glyceraldehyde-3-phosphate dehydrogenase (G3PDH) was used as a control. The probes used had the sequences given by Seq. ID. Nos. 60–63. The RNA blots were hybridized with human IGFBP_2 probe labeled with [$^{32}$P]dCTP by random primer labeling. Washing and densitometric analysis was carried out. After detecting the IGFBP-2 encoding RNA, the membranes were re-probed using human G3PDH probes to verify integrity.

Seq. ID No. 1 was most effective, causing up to 80–90% reduction in IGFBP-2 mRNA levels. Seq ID. Nos. 2 and 3 were also effective, albeit less so, causing a decrease of about 50%.

Example 2

The LNCaP model is an androgen-sensitive, PSA-secreting, human prostate cancer cell line that can be induced to form tumors in athymic mice under a variety of conditions. Like in human prostate cancer, serum PSA levels in this model are regulated by androgen and are directly proportional to tumor volume. After castration, serum and tumor-cell PSA levels decrease up to 80% and remain suppressed for 3–4 weeks. Beginning 4 weeks after castration, however, PSA production gradually increases above pre-castrate levels in the absence of testicular androgens, heralding the onset of androgen-independent progression. The pattern of changes in gene expression after castration in the LNCaP model is similar to that in the Shionogi system, with increased expression of Bcl-2, TRPM-2, and IGFBP-2 following castration of mice bearing LNCaP tumors. It is important to stress that many of the changes in gene expression in the LNCaP and Shionogi models also occur in human prostate cancer (e.g, Bcl-2, clusterin, IGFBP's, PSA, Bcl-xL), which validates their use as models of the human disease for functional genomics and preclinical proof of principle experiments. In the study leading to the present invention, we initially characterized changes of IGFBP expression in the LNCaP tumor model after castration and during AI progression. Northern blot analyses showed that IGFBP-2 levels increased up to 2–3 fold in androgen-independent tumors compared to androgen dependent tumors prior to castration, suggesting IGFBP-2 increases may be associated with the development of the androgen-independent phenotype (FIG. 1).

Example 3

The Shionogi tumor model mimics human prostate cancer and provides a very useful model for the evaluation of the ability of compounds to delay the onset of androgen-independence. Despite complete tumor regression after castration, rapidly growing androgen-independent Shionogi tumors invariably recur after one month, which provides a reliable end point to evaluate agents which can delay the progression to androgen-independence. In the study leading to the present invention, we initially characterized changes of IGFBP expression in the Shionogi tumor model after castration and during AI progression. Northern blot analyses were used to characterize changes in IGFBP mRNA expression in AD intact tumors before castration, regressing tumors 4 and 7 days after castration, and AI recurrent tumors 28 days after castration. IGFBP-2 levels increased up to 2–3 fold in androgen-independent tumors compared to androgen dependent tumors prior to castration, suggesting IGFBP-2 increases may be associated with the development of the androgen-independent phenotype.

Example 4

Figure 2:
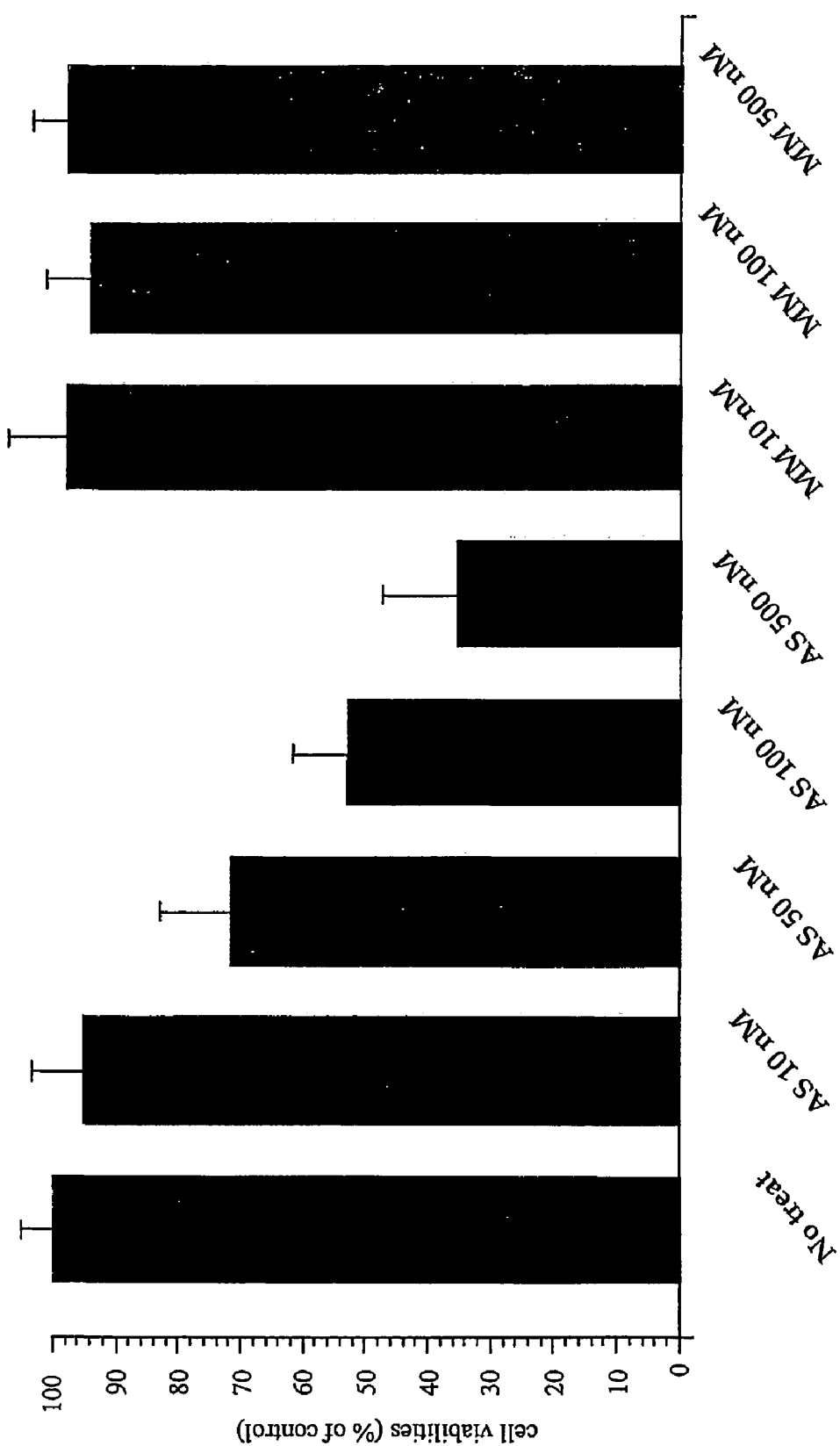
FIG. 2 depicts in vitro levels of viable human prostate LNCaP cells showing dose-dependent decreases in cell number after antisense IGFBP-2 treatment.

Treatment of human LNCaP cells with IGFBP-2 ASO (Seq. ID. No. 1) resulted in dose-dependent and sequence-specific downregulation of IGFBP-2 mRNA and protein levels. IGFBP-2 levels were decreased by 90% after treatment with 500 nM IGFBP-2 ASO (Seq. ID. No. 1). Cell viability also decreased in a dose-dependent manner. (FIG. 2).

Example 5

Treatment of human LNCaP tumor cells with IGFBP-2 ASO (Seq. ID. No. 1) decreased target mRNA and protein levels greater than 90% and resulted in greater than 50% growth inhibition in a time- and dose-dependent manner (FIG. 2).

Example 6

Figure 3A:
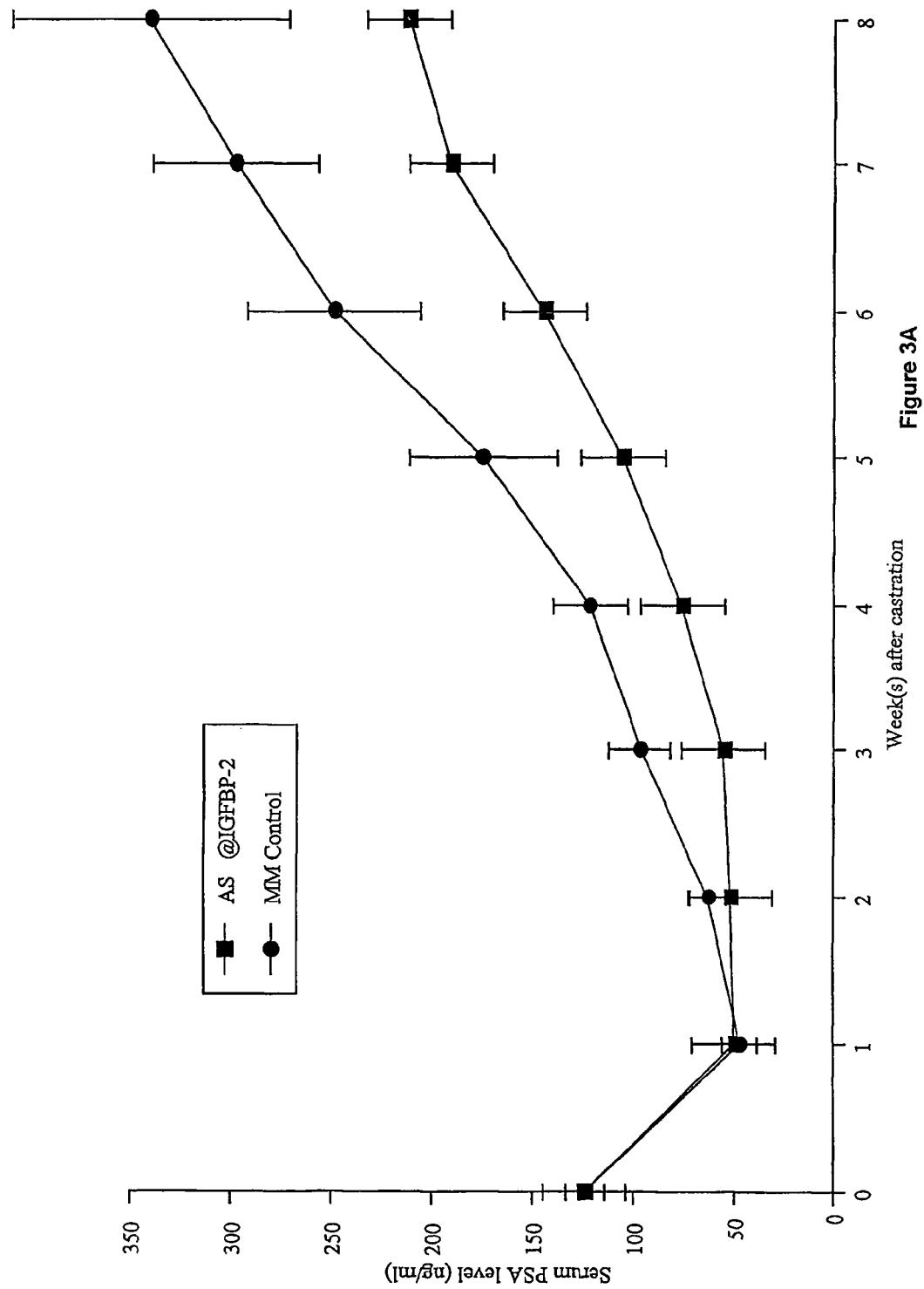
FIGS. 3*a* and 3*b* show that treatment of LNCaP-tumor bearing mice after castration with IGFBP-2 ASO's reduces tumor growth rates and rises in serum PSA and delays time to androgen independent progression.
Figure 3B:
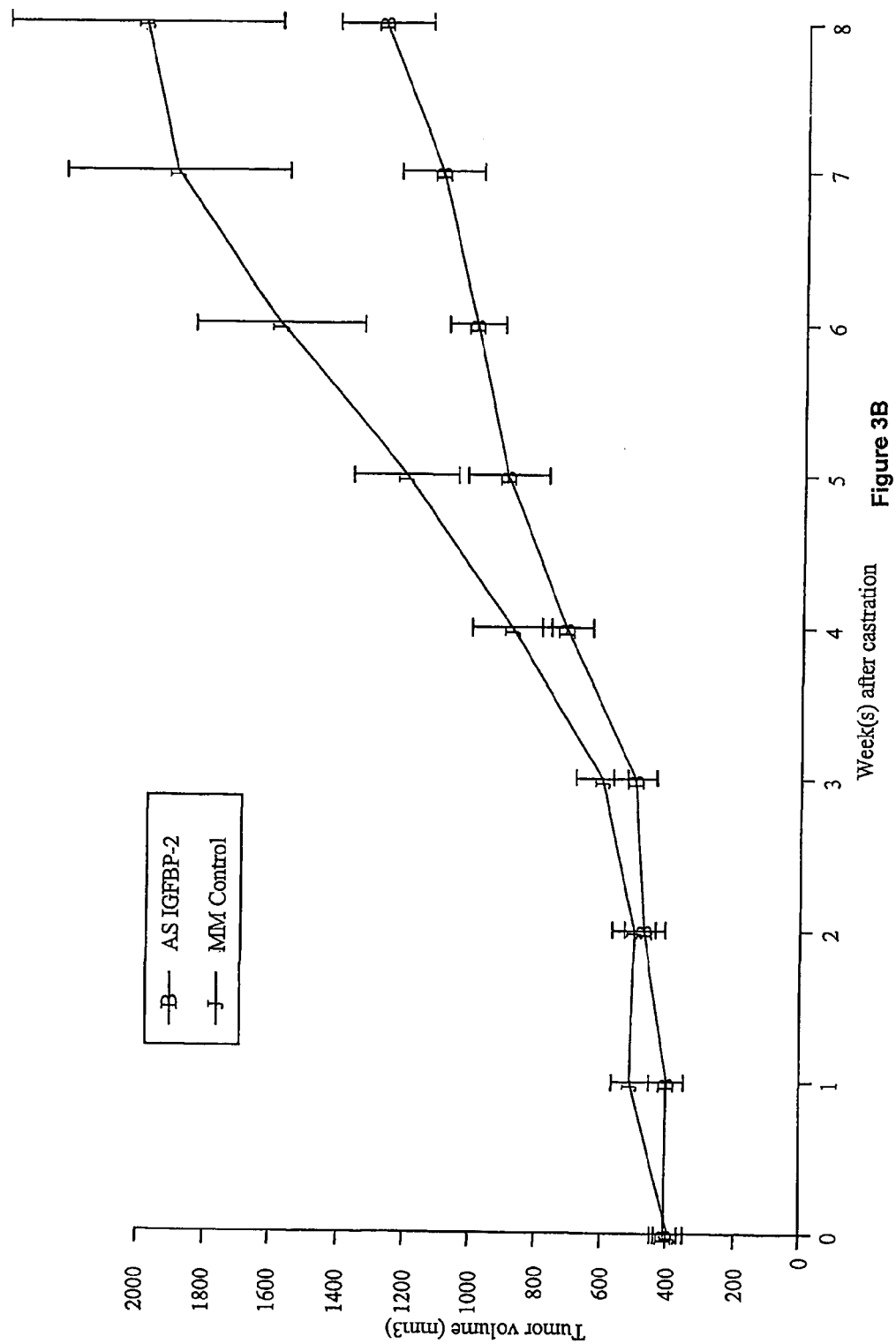

Systemic administration of IGFBP-2 ASO (Seq. ID. No. 1) in mice bearing human LNCaP prostate tumors after castration significantly delayed the growth of AI recurrent tumors and time to sacrifice. LNCaP tumor growth and rises in serum PSA were both significantly delayed in mice treated with IGFBP-2 ASO's compared to controls treated with mismatch ASO's (FIGS. 3a and 3b). These findings provide the first evidence that upregulation of IGFBP-2 after castration enhances the mitogenic activity of IGF-I, and illustrates a potential use for IGFBP-2 ASO therapy for prostate cancer.

Example 7

Treatment of human LNCaP tumor cells with IGFBP-2 ASO (Seq. ID. No. 1) decreased target mRNA and protein levels greater than 90% and resulted in greater than 50% growth inhibition in a time- and dose-dependent manner, an effect that could not be reversed by exogenous IGF-I (FIG. 4). IGFBP-2 ASO (Seq. ID. No. 1) plus IGF-I antibody treatment had additional inhibitory effect on LNCaP tumor cell growth in vitro.

Example 8

To examine the effects on cell cycle regulation of decreases in IGFBP-2 levels by IGFBP-2 ASO treatment, changes in cyclin D1 levels were evaluated in LNCaP cells after treatment with IGFBP-2 ASO (Seq. ID. No. 1). Western analysis demonstrated a greater than 50% decrease in cyclin D1 after IGFBP-2 ASO (Seq. ID. No. 1) treatment, illustrating that decreases in IGFBP-2 by ASO treatment inhibits IGF-I signaling and results in cell cycle arrest. Apoptosis induction after IGFBP ASO treatment was also shown by LNCaP cell cycle analysis by flow cytometry after treatment with IGFBP-2 ASO. LNCaP cells were treated daily with IGFBP-2 ASO or mismatch control oligonucleotide with or without 1 nM DHT (dihydrotestoterone) for 2 days. Table 1 shows cell populations in each phase (Sub G1–G0, G1–G0, S, and G2+M) in % for the various treatments. Each datum represents the mean value of triplicate experiments. After IGFBP-2 ASO treatment, the percent of cells in Sub G1–G0 increased 3-fold (p<0.05), while percent of cells in G2+M decreased by 50%.

TABLE 1

| Treatment | Sub G1-G0 | G1-G0 | S | G2 and M |
|---|---|---|---|---|
| No TX DHT (+) | 8.5 | 82 | 4.2 | 5 |
| IGFBP-2 ASO DHT (+) | 28 | 65.4 | 2.9 | 3.8 |
| MM control DHT (+) | 9.5 | 81.6 | 4.4 | 5.8 |
| No TX DHT (−) | 7.9 | 79.1 | 4.5 | 8.6 |
| IGFBP-2 ASO DHT (−) | 24.6 | 68.8 | 2 | 4.6 |
| MM control DHT (−) | 9 | 79.4 | 3.5 | 8.2 |

Example 9

Metastatic prostate and breast cancer frequently invade bony tissue. Treatment of such metastases is very difficult, and progression of the cancer into the bone generally indicates a poor prognosis for long term survival. Thus, it would be desirable to have a methodology for inhibiting or delaying this progression. It was logical to assume that since IGF-I and IGFBP-2 are important factors for growth of IGF-I sensitive cancer, including in particular prostate and breast cancer, that the presence of high levels of IGFBP-2 in bone could be an important mechanism for promoting the growth and progression of metastatic lesions. Accordingly, Western analysis was performed on samples of primary human bone tissue cultures. This experiment confirmed the presence of high levels of IGFBP-2 in bone. inhibition of these levels using antisense IGFBP-2 ODN in accordance with the invention should provide an effective therapy for inhibiting or delaying the progression of metastatic lesions in the bone.

TABLE 2

| | |
|---|---|
| Seq. ID No. 1 | GCAGCCCACTCTCGGCAGCAT |
| Seq. ID No. 2 | CGCCCAGTAGCAGCAGCAGCA |
| Seq. ID No. 3 | TCCCGGAACACGGCCAGCTCC |
| Seq. ID No. 4 | CAGCCCACTCTCGGCAGCAT |
| Seq. ID No. 5 | GGGCAGCGGAACAGCACCTC |
| Seq. ID No. 6 | CCCGGCTCCCGGACGAGCTC |
| Seq. ID No. 7 | GCCTGCAGGGGCAGCTCGGA |
| Seq. ID No. 8 | ACGTGGTTCTCCACCAGGCC |
| Seq. ID No. 9 | CCCATCTGCCGGTGCTGCTC |
| Seq. ID No. 10 | AGGCGCATGGTGGAGATCCG |
| Seq. ID No. 11 | CACTCCCCACGCTGCCCGTT |
| Seq. ID No. 12 | CGCTGGGTGTGCACCCCGCG |
| Seq. ID No. 13 | TGTCAGAACTGGAAAATCCT |
| Seq. ID No. 14 | GCAGCCCACTCTCGGCAGCAT |
| Seq. ID No. 15 | CAGTAGCAGCAGCAGCAGCGG |
| Seq. ID No. 16 | TGTGCAGGGCGGGCAGCGGAA |
| Seq. ID No. 17 | GCCCTCCACCGGGGCGCACAC |
| Seq. ID No. 18 | GCCCGGGTGGGGATAGCAGCG |
| Seq. ID No. 19 | CGCCTGCAGGGGCAGCTCGGA |
| Seq. ID No. 20 | AGTGCCCTCGCCCATGACCAG |
| Seq. ID No. 21 | CTCCGGGCTGGCGCCATACTC |
| Seq. ID No. 22 | ATCGCCATTGTCTGCAACCTG |
| Seq. ID No. 23 | CAGGCCTCCTTCTGAGTGGTC |
| Seq. ID No. 24 | GCTGTCCACGTGGTTCTCCAC |
| Seq. ID No. 25 | CCCGCCCAACATGTTCATGGT |
| Seq. ID No. 26 | CTTCCGGCCAGCACTGCCTCC |
| Seq. ID No. 27 | CTTCATACCCGACTTGAGGGG |
| Seq. ID No. 28 | CTCCCGGAACACGGCCAGCTC |
| Seq. ID No. 29 | CCGGTGCTGCTCAGTGACCTT |
| Seq. ID No. 30 | CTTGCCACCCTTGCCCATCTG |
| Seq. ID No. 31 | CTCCTCCAGGCCAAGGTGATG |
| Seq. ID No. 32 | GGGTGGTCGCAGCTTCTTGGG |
| Seq. ID No. 33 | TTGGCAGGGAGTCCTGGCAGG |
| Seq. ID No. 34 | CAGGACCTGGTCCAGTTCCTG |
| Seq. ID No. 35 | GCGCATGGTGGAGATCCGCTC |
| Seq. ID No. 36 | AGGGCCCCGCTCATCCGGAAG |
| Seq. ID No. 37 | CAGGGAGTAGAGGTGCTCCAG |
| Seq. ID No. 38 | CTTGTCACAGTTGGGGATGTG |
| Seq. ID No. 39 | TTTGAGGTTGTACAGGCCATG |
| Seq. ID No. 40 | GTTCAGAGACATCTTGCACTG |
| Seq. ID No. 41 | CCAGCACTCCCCACGCTGCCC |
| Seq. ID No. 42 | CCCGGTGTTGGGGTTCACACA |
| Seq. ID No. 43 | GGGGGCTCCCTGGATCAGCTT |
| Seq. ID No. 44 | CTCGGGGTCCCCCCGGATGGT |
| Seq. ID No. 45 | CTCATTGTAGAAGAGATGACA |
| Seq. ID No. 46 | CGCCCAGTAGCAGCAGCAGCA |
| Seq. ID No. 47 | TCCCGGAACACGGCCAGCTCC |
| Seq. ID No. 48 | CAGCCCACTCTCGGCAGCAT |
| Seq. ID No. 49 | GGGCAGCGGAACAGCACCTC |
| Seq. ID No. 50 | CCCGGCTCCCGGACGAGCTC |
| Seq. ID No. 51 | ACGTGGTTCTCCACCAGGCC |
| Seq. ID No. 52 | CCCATCTGCCGGTGCTGCTC |
| Seq. ID No. 53 | AGGCGCATGGTGGAGATCCG |
| Seq. ID No. 54 | CACTCCCCACGCTGCCCGTT |
| Seq. ID No. 55 | CGCTGGGTGTGCACCCCGCG |

TABLE 2-continued

| Seq. ID No. 56 | TGTCAGAACTGGAAAATCCT |
| Seq. ID No. 57 | GCAGCCCACTGTCCGCAGCAT |
| Seq. ID No. 58 | CGCGCACTAGCAGCAGCAGCA |
| Seq. ID No. 59 | TCCCGGAACTGCCCCAGCTCC |
| Seq. ID No. 60 | ACAATGGCGGATGACCACTCAGA |
| Seq. ID No. 61 | ACAGCACCATGAACATGTTTG |
| Seq. ID No. 62 | TGCTTTTAACTCTGGTAAAGT |
| Seq. ID No. 63 | ATATTTGGCAGGTTTTTCTAGA |

The invention claimed is:

1. A method for treating a hormone-responsive cancer in an individual suffering from hormone-responsive cancer, comprising administering to the individual a composition comprising an antisense oligonucleotide which targets IGFBP-2 and thereby inhibits expression of IGFBP-2 by hormone-regulated tumor cells, whereby growth and metastatic progression of the cancer is inhibited or delayed in the individual.

2. The method of claim 1, wherein the composition is administered to the individual after initiation of hormone-withdrawal to induce apoptotic cell death of hormone-responsive cancer cells in the individual, and thereby delays the progression of hormone-responsive cancer cells to a hormone-independent state in the individual.

3. A method for delaying progression of hormone-regulated tumor cells to an hormone-independent state comprising the step of treating hormone-sensitive tumor cells with an antisense oligonucleotide which targets IGFBP-2 and thereby inhibits expression of IGFBP-2 by the tumor cells, whereby progression of the tumor cells to androgen independence is delayed.

4. The method of claim 1 wherein the individual is a human.

5. The method of claim 1 wherein the cancer treated is prostate cancer and the tumor cells are prostatic tumor cells.

6. The method of claim 1 wherein the cancer treated is breast cancer and the tumor cells are breast cancer cells.

7. The method of claim 5, wherein the individual is human.

8. The method of claim 6, wherein the individual is human.

* * * * *